(12) United States Patent
Fujii et al.

(10) Patent No.: US 8,803,010 B2
(45) Date of Patent: Aug. 12, 2014

(54) WEIGHT MEASURING APPARATUS FOR MEASURING A WEIGHT OF FLUIDS

(75) Inventors: Junya Fujii, Hiroshima (JP); Shogo Kamito, Hiroshima (JP); Masaki Furukoshi, Tokyo (JP)

(73) Assignee: JMS Co., Ltd., Hiroshima (JP)

( * ) Notice: Subject to any disclaimer, the term of this patent is extended or adjusted under 35 U.S.C. 154(b) by 302 days.

(21) Appl. No.: 13/379,790

(22) PCT Filed: Jun. 23, 2010

(86) PCT No.: PCT/JP2010/004173
§ 371 (c)(1),
(2), (4) Date: Dec. 21, 2011

(87) PCT Pub. No.: WO2010/150536
PCT Pub. Date: Dec. 29, 2010

(65) Prior Publication Data
US 2012/0097459 A1    Apr. 26, 2012

(30) Foreign Application Priority Data

Jun. 24, 2009 (JP) .................................. 2009-150358

(51) Int. Cl.
| A61M 1/14 | (2006.01) |
| G01G 23/18 | (2006.01) |
| G01G 17/04 | (2006.01) |
| G01G 21/16 | (2006.01) |
| G01G 3/14 | (2006.01) |
| A61M 1/34 | (2006.01) |
| A61M 1/16 | (2006.01) |

(52) U.S. Cl.
CPC .............. *G01G 3/1412* (2013.01); *G01G 17/04* (2013.01); *A61M 1/341* (2013.01); *A61M 1/1643* (2013.01); *A61M 2205/3393* (2013.01); *Y10S 128/13* (2013.01)
USPC ............... 177/45; 177/199; 177/245; 604/65; 604/500; 128/DIG. 13

(58) Field of Classification Search
USPC ........ 177/45, 199, 245; 128/DIG. 13; 604/65, 604/500
See application file for complete search history.

(56) References Cited

U.S. PATENT DOCUMENTS

| 4,650,464 | A | * | 3/1987 | Ruiz et al. ..................... 604/500 |
| 5,112,319 | A | * | 5/1992 | Lai ................................ 604/246 |

(Continued)

FOREIGN PATENT DOCUMENTS

| CN | 2303283 | 1/1999 |
| CN | 101421594 | 4/2009 |

(Continued)

OTHER PUBLICATIONS

Machine translation of JP 2007-285830 from the JPO website. Dec. 13, 2013.*

(Continued)

*Primary Examiner* — Randy W Gibson
(74) *Attorney, Agent, or Firm* — Wenderoth, Lind & Ponack, L.L.P.

(57) ABSTRACT

A weight measuring apparatus can ensure safety even if a trouble or deterioration of measurement accuracy occurs. The weight measuring apparatus (10) measures a weight of fluids and includes the followings. A first arm (110) has a first fitting (111) to fit a supply fluid container (20). A second arm (120) is connected to the first arm (110) and has a second fitting (121) to fit a filtrate container (30). A third arm (130) is connected to the second arm (120). A first measuring device (220) measures, as a first total weight, a total weight of the supply fluid container (20) and the filtrate container (30) based on a change of the second arm (120). A second measuring device (230) measures, as a second total weight, the total weight based on a change of the third arm (130). An alarm (300) alarms, when the first and second total weights have different values having a difference equal to or greater than a predetermined value.

5 Claims, 8 Drawing Sheets

(56) References Cited

U.S. PATENT DOCUMENTS

| | | |
|---|---|---|
| 5,539,157 A | 7/1996 | Kobayashi et al. |
| 5,679,245 A | 10/1997 | Manica |
| 5,762,805 A | 6/1998 | Truitt et al. |
| 5,776,345 A | 7/1998 | Truitt et al. |
| 5,910,252 A | 6/1999 | Truitt et al. |
| 7,977,586 B2 | 7/2011 | Fujii et al. |
| 2009/0276099 A1 | 11/2009 | Fujii et al. |

FOREIGN PATENT DOCUMENTS

| | | |
|---|---|---|
| DE | 299 17 274 | 2/2000 |
| EP | 2 019 296 | 1/2009 |
| JP | 55-40954 | 3/1980 |
| JP | 4-369437 | 12/1992 |
| JP | 2006-105734 | 4/2006 |
| JP | 2007-285830 | 11/2007 |

OTHER PUBLICATIONS

Extended European Search Report issued Oct. 14, 2013 in corresponding European patent application No. 10791858.3.

International Search Report issued Jul. 27, 2010 in International (PCT) Application No. PCT/JP2010/004173.

* cited by examiner

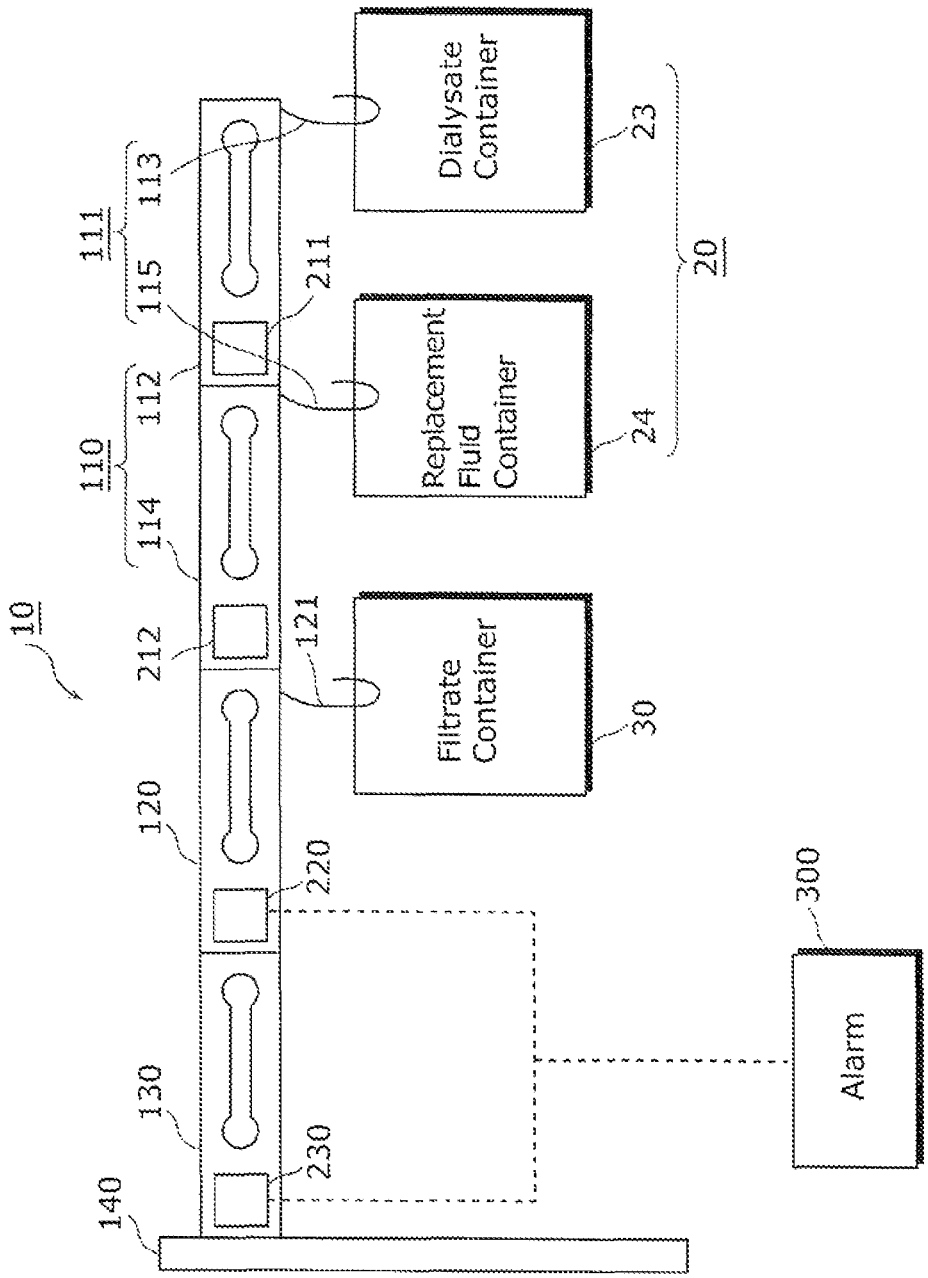

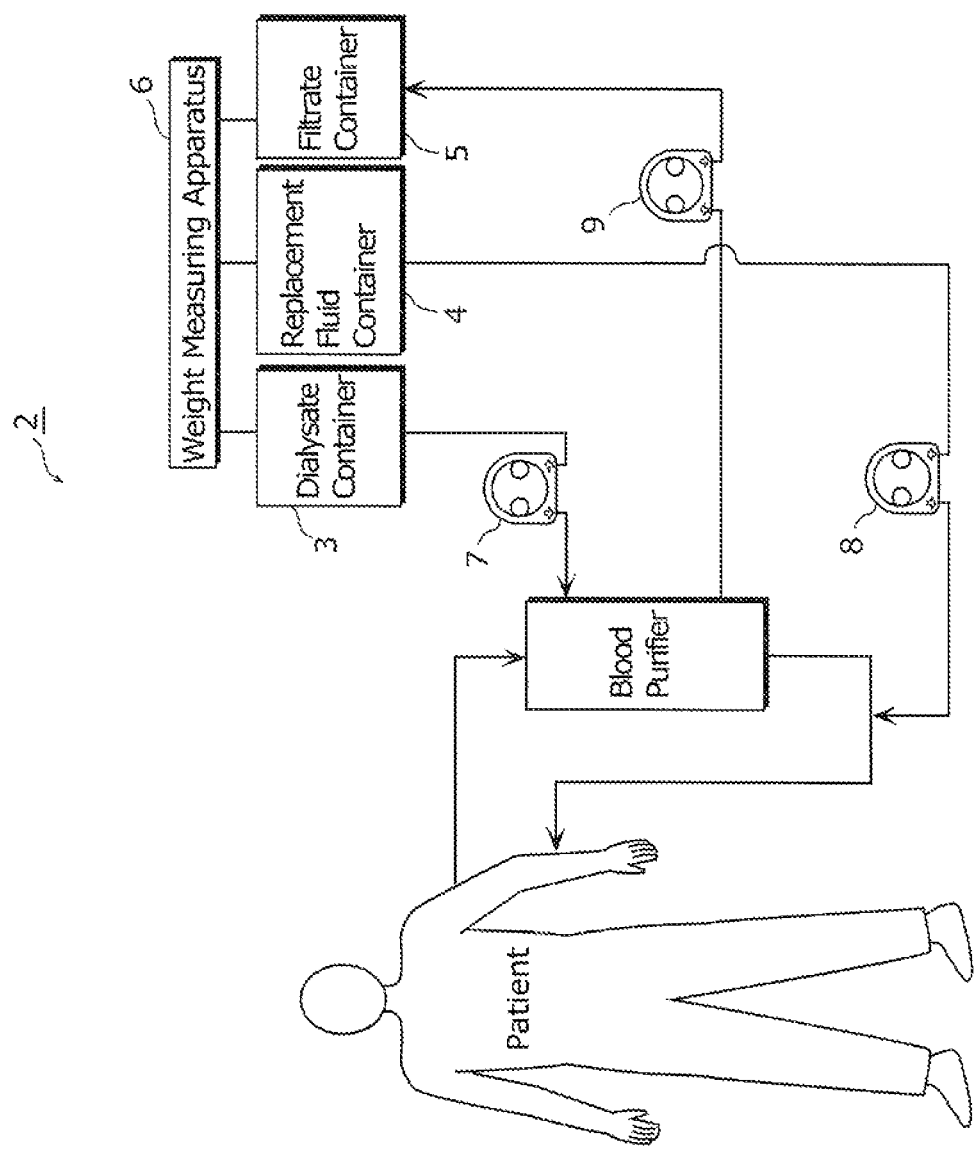

WEIGHT MEASURING APPARATUS FOR MEASURING A WEIGHT OF FLUIDS

TECHNICAL FIELD

The present invention relates to a weight measuring apparatus that includes containers containing fluids and that measures a weight of the fluids.

BACKGROUND ART

Conventionally, in order to purify blood of patients with renal function insufficiency, for example, medical treatments using Continuous Hemofiltration (CHF), Continuous Hemodiafiltration (CHDF), and/or the like have been performed.

In the CHF, blood taken from a patient is provided to a blood is purifier having a semipermeable membrane (hemofiltration membrane) for hemofiltration, and then filtered by the hemofiltration membrane to generate purified blood. The purified blood is returned to the patient body, and waste products (electrolytic substance such as urea and sodium chloride, for example) and solvent (water) resulting from the hemofiltration are discarded. In parallel, a predetermined replacement fluid is supplied to blood of the patient so as to supplement a decrease in solvent of the blood. The above processing is performed continually and slowly. In the CHF, waste products and solvent which are taken from blood in order to be discarded are called filtrate.

On the other hand, the CHDF is a method of improving a capability of removing small molecules in the CHF. In the CHDF, dialysis as well as the CHF are performed. More specifically, in the CHDF, a blood purifier having a dialysis membrane in addition to a hemofiltration membrane is used. The blood purifier is provided also with dialysate. Waste products still included in the purified blood after hemofiltration are sent to the dialysate through the dialysis membrane, so that the waste products can be removed from the blood. Then, the blood purified by the hemofiltration and the dialysis is as returned to the patient body and a replacement fluid is supplied to the blood of the patient. The above processing is performed continuously and slowly. In the CHDF, waste product and solvent which are taken from the blood during hemofiltration, and used dialysate are called filtrate.

In the meanwhile, a change in an amount of blood in a patient body affects patient's condition. In order to avoid such situations, it is necessary to keep a balance between (a) a flow rate of blood taken from the patient and (b) a total flow rate of blood returned to the patient and replacement fluid supplied to the patient. More specifically, it is necessary to continuously perform high-accuracy fluid control for 24 hours a day, so that a total amount of decrease in the dialysate and the replacement fluid is always equal to an amount of increase in the filtrate.

However, sending of the dialysate, the replacement fluid, and the filtrate required a plurality of pumps. If a difference of an amount of fluid sent by a single pump is 10%, a total difference of an amount of fluid sent by two pumps is 20% at maximum, for example. The difference is not allowable in treatments demanding the above-described fluid balance.

Therefore, there has been conceived a weight measuring apparatus that keeps, with high accuracy, balance between (a) a total amount of decrease in the dialysate and the replacement fluid and (b) an amount of increase in the filtrate, when the above-described blood purification treatment is performed (refer to Patent Reference 1, for example).

FIG. 10 is a diagram for explaining the conventional weight measuring apparatus.

As shown in FIG. 10, a blood purification apparatus 2 includes a conventional weight measuring apparatus 6 having a plurality of pumps 7 to 9. The pumps 7 to 9 send dialysate contained in a dialysate container 3, replacement fluid contained in a replacement fluid container 4, and filtrate contained in a filtrate container 5, respectively. The dialysate container 3, the replacement fluid container 4, and the filtrate container 5 are hanged by the weight measuring apparatus 6 to measure a total weight of the three containers. The pumps 7 to 9 are thereby controlled to keep a predetermined valued of the total weight.

Thereby, it is possible to control (a) a total amount of decrease in the dialysate and the replacement fluid and (b) an amount of increase in the filtrate to be equal to each other. In other words, in order to keep, with high accuracy, balance between (a) a total amount of decrease in the dialysate and the replacement fluid and (b) an amount of increase in the filtrate, the method of controlling the pumps 7 to 9 to keep the predetermined value of the total weight of the three containers is prefer to the method of measuring weights of the respective dialysate container 3, replacement fluid container 4, and filtrate container 5 and then controlling the pumps 7 to 9.

CITATION LIST

Patent Literature

[PTL] Japanese Unexamined Patent Application Publication No. 2007-285830.

DISCLOSURE OF INVENTION

Problems that Invention is to Solve

However, the conventional weight measuring apparatus has a problem that weights of the containers are measured even if a trouble or deterioration of measurement accuracy occurs, and therefore safety of blood purification cannot be ensured.

The measurement results of the weight measuring apparatus significantly influence medical treatments. Therefore, the weight measuring apparatus needs to have a high accuracy by which an error in the measurement is always 1% or less. Any failure of such high-accuracy measurement of the weight measuring apparatus is fatal. However, sometimes nobody notices such a trouble or deterioration of measurement accuracy and the measurement is continued, which results in failure of safe treatments.

In order to address the above-described conventional problems, an object of the present invention is to provide a weight measuring apparatus that ensures safety even if a trouble, deterioration of measurement accuracy, or the like occurs.

Means to Solve the Problems

In accordance with an aspect of the present invention for achieving the object, there is provided a weight measuring apparatus to which containers containing fluids are fit, the weight measuring apparatus measuring a weight of the fluids, the weight measuring apparatus including: a first arm having a first fitting to fit a first container containing a first fluid; a second arm having a second fitting to fit a second container containing a second fluid, the second arm being connected to the first arm; a first measuring device that measures, as a first total weight, a total weight based on a change of the second arm, the total weight being a total of a weight of the first container fit by the first fitting and a weight of the second container fit by the second fitting; a third arm connected to the second arm; a second measuring device measuring, as a second total weight, the total weight based on a change of the third arm; and an alarm alarming, when the first total weight and the second total weight have different values having a difference equal to or greater than a predetermined value.

With the above structure, both the first measuring device and the second measuring device measure a total weight of the first container and the second container. Therefore, the two measuring devices can perform mutual monitoring. In addition, if values measured by the two measuring devices are different, alarming is performed. Therefore, even if the first measuring device or the second measuring device has a trouble, deterioration of measuring accuracy, or the like, it is possible to notice the trouble, deterioration, or the like. As a result, safety of the blood purification is ensured.

It is preferable that the alarm includes: a first change amount calculation unit configured to calculate a first change amount that is an amount having changed since an initial state of the first total weight; a second change amount calculation unit configured to calculate a second change amount that is an amount having changed since an initial state of the second total weight; a difference calculation unit configured to calculate a difference between the first change amount and the second change amount; a difference determination unit configured to determine whether or not the difference is equal to or greater than the predetermined value; and an alarm signal output unit configured to issue an alarm signal to alarm, when the difference determination unit determines that the difference is equal to or greater than the predetermined value.

With the above structure, when the first change amount and the second change amount have different values having a difference equal to or greater than the predetermined value, the alarm signal is issued. In receiving the alarm signal, the blood purification apparatus can display alarm notification on a display screen, stop the blood purification, or adjust flow rates of the fluids. Therefore, even if the first measuring device or the second measuring device has a trouble, deterioration of measuring accuracy, or the like, it is possible to immediately notice the trouble, deterioration, or the like. As a result, safety of the blood purification is ensured.

Effects of the Invention

Accordingly, the present invention can provide a weight measuring apparatus that includes containers containing fluid and measures a weight of the containers, and that can ensure safety of the blood purification even if a trouble or deterioration of measurement accuracy occurs.

BRIEF DESCRIPTION OF DRAWINGS

FIG. 9 is a diagram of a weight measuring apparatus according to a second variation of the embodiment of the present invention.

FIG. 10 is a diagram of a conventional weight measuring apparatus.

BEST MODE FOR CARRYING OUT THE INVENTION

The following describes an embodiment of the present invention with reference to the drawings.

Figure 1:
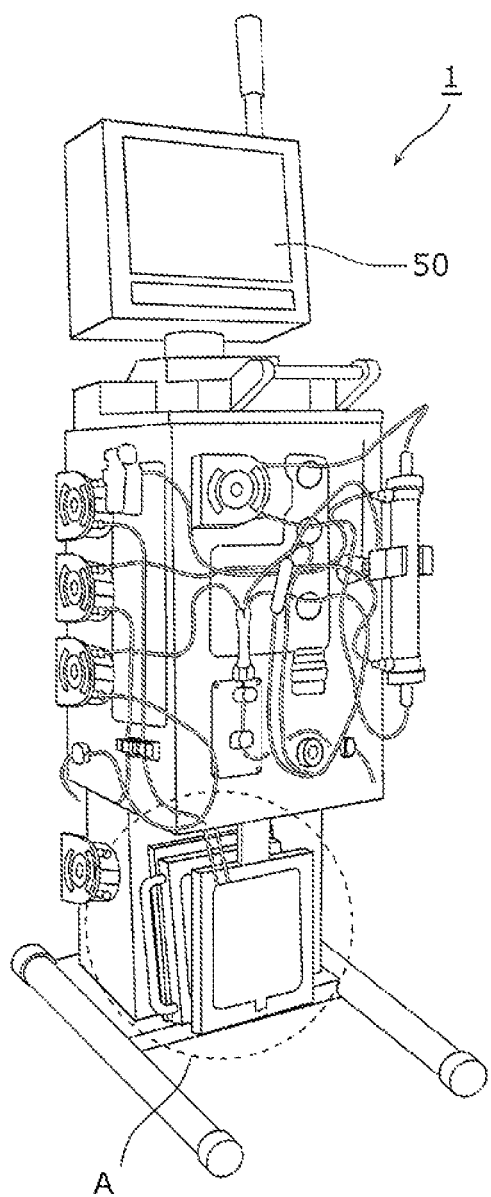
FIG. 1 is an external view of a blood purification apparatus according to an embodiment of the present invention.

FIG. 1 is an external view of a blood purification apparatus 1 according to the embodiment of the present invention.

The blood purification apparatus 1 is an apparatus that removes waste products from blood of a patient having, for example, a renal function insufficiency, in blood purification treatments for purifying the blood.

More specifically, the blood purification apparatus 1 removes waste products from the blood by using dialysate and thereby discharges filtrate. In addition, the blood purification apparatus 1 supplies a replacement fluid to the blood so as to supplement a decrease in solvent of the blood. The dialysate, the replacement fluid, and the filtrate are contained in respective different containers. A weight measuring apparatus measures weights of the containers to keep balance between (a) a total flow rate of the dialysate and replacement fluid to be used and (b) a flow rate of the filtrate to be discarded.

The measurement results of the weight measuring apparatus are displayed on a display unit 50. Examples of the display unit 50 are a Cathode-Ray Tube (CRT), a Liquid Crystal Display (LCD), and the like.

This weight measuring apparatus is provided at a position indicated by A in FIG. 1. The following describes the weight measuring apparatus in more detail.

Figure 2:
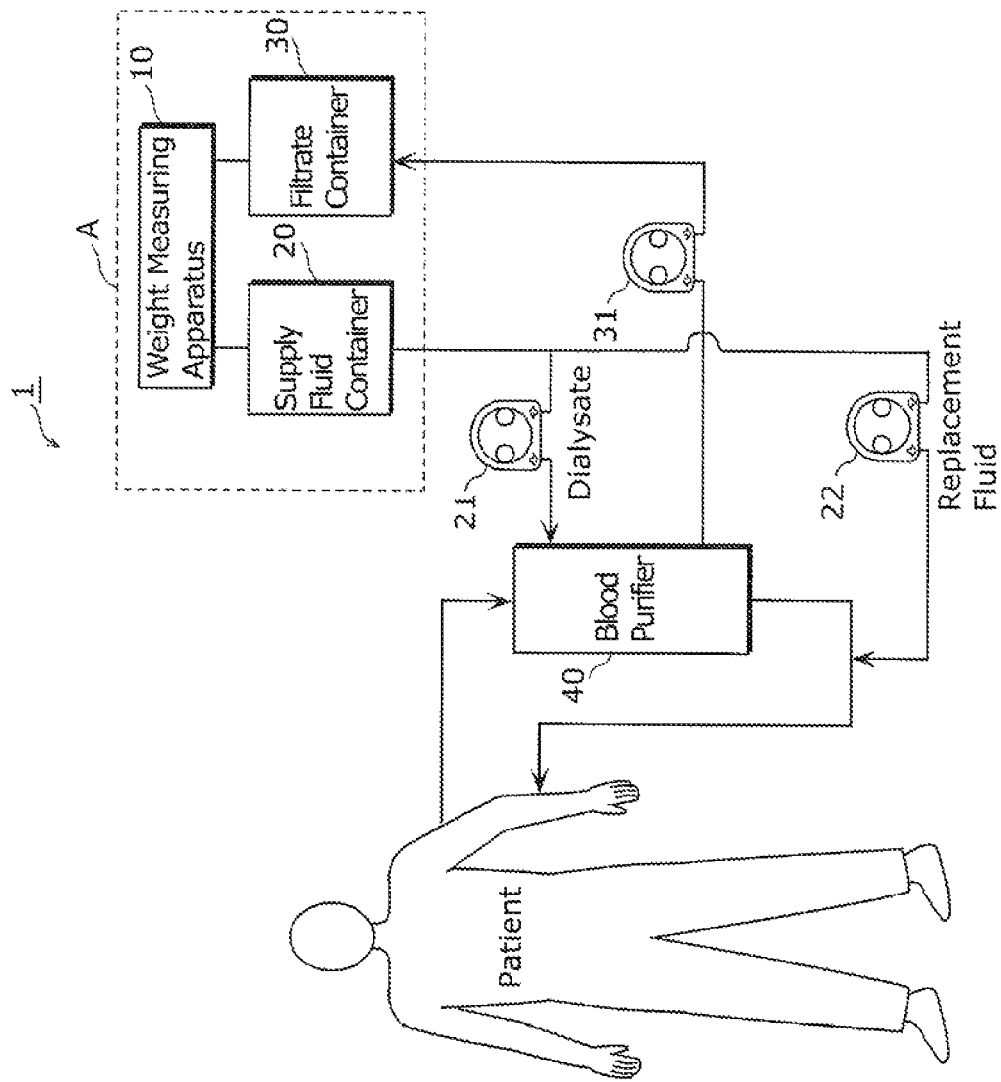
FIG. 2 is a block diagram of the blood purification apparatus according to the embodiment of the present invention.

FIG. 2 is a block diagram showing a structure of the blood purification apparatus 1 according to the embodiment of the present invention.

As shown in FIG. 2, the blood purification apparatus 1 includes a weight measuring apparatus 10, a dialysate pump 21, a replacement fluid pump 22, a filtrate pump 31, and a blood purifier 40. The weight measuring apparatus 10 is provided at the position indicated by A in FIG. 1.

The blood purifier 40 is equipment for purifying blood. In more detail, the blood purifier 40 has a bundle of a large number of hollow fibers penetrated in the cylindrical inside of the blood purifier 40, and blood is introduced to the inside of the hollow fibers, so that via a filter formed by the hollow fibers the blood indirectly contacts with dialysate flowing in the cylindrical inside of the blood purifier 40. Waste products in the blood, such as urea, uric acid, creatine, and redundant water, are discharged to the dialysate, while electrolyte in the dialysate enters the blood, using principles of diffusion, ultrafiltration, and an osmotic pressure.

The dialysate is a chemical fluid used to exchange substances between the dialysate and blood in the blood purifier 40. The replacement fluid is a chemical fluid used to supply water and electrolyte into blood which have been lost from the blood passing through the blood purifier 40. Each of the dialysate and the replacement fluid is a chemical fluid such as an isotonic fluid adjusted to have an osmotic pressure and electrolyte which are equal to those of a body fluid. Hereinafter, the supply fluid is a collective term of a replacement fluid and a dialysate.

The weight measuring apparatus 10 includes containers containing fluids for blood purification, and measures a weights of the fluids. Here, the fluids for blood purification are supply fluids (a dialysate and a replacement fluid) and a filtrate. In other words, a supply fluid container 20 containing the supply fluid and a filtrate container 30 containing the filtrate are hanged by the weight measuring apparatus 10, and the weight measuring apparatus 10 measures weights of the containers. The weight measuring apparatus 10 will be described in more detail later.

In accordance with the aspect of the present invention, the supply fluid corresponds to the "first fluid" and the supply fluid container 20 corresponds to the "first container". In addition, in accordance with the aspect of the present invention, the filtrate corresponds to the "second fluid" and the filtrate container 30 corresponds to the "second container".

The dialysate pump 21 is a pump that sends the supply fluid (dialysate) contained in the supply fluid container 20 to the blood purifier 40. The dialysate pump 21 adjusts an amount of sending dialysate by controlling the number of rotations of the dialysate pump 21.

The replacement fluid pump 22 is a pump that sends the supply fluid (replacement fluid) contained in the supply fluid container 20 to the blood that is at an exit of the blood purifier 40 to be returned to the patient. The replacement fluid pump 22 adjusts an amount of sending replacement fluid by controlling the number of rotations of the replacement fluid pump 22.

The filtrate pump 31 is a pump that sends a filtrate including waste products to be discharged by the blood purifier 40, and stores the filtrate into the filtrate container 30. The filtrate pump 31 adjusts an amount of sending filtrate by controlling the number of rotations of the filtrate pump 31.

With the above structure, when the dialysate pump 21 or the replacement fluid pump 22 sends the supply fluid, the supply fluid contained in the supply fluid container 20 is reduced. On the other hand, when the filtrate pump 31 sends the filtrate, the filtrate contained in the filtrate container 30 is increased. This means that an amount of decrease in the supply fluid contained in the supply fluid container 20 is adjusted by controlling a flow rate of the dialysate pump 21 or the replacement fluid pump 22. On the other hand, an amount of increase in the filtrate in the filtrate container 30 is adjusted by controlling a flow rate of the filtrate pump 31.

The following describes the structure of the weight measuring apparatus 10 in more detail.

Figure 3:
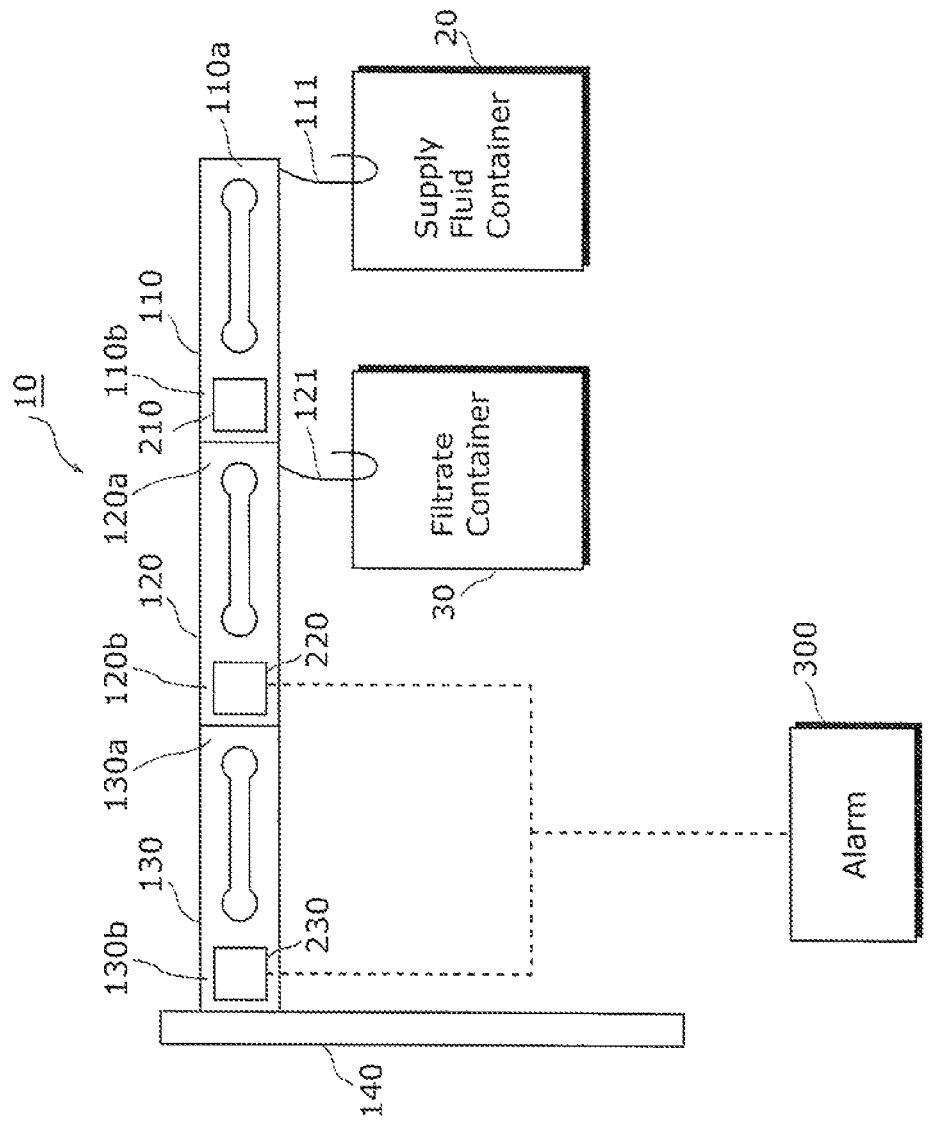
FIG. 3 is a diagram showing details of a structure of a weight measuring apparatus according to the embodiment of the present invention.

FIG. 3 is a diagram showing details of the structure of the weight measuring apparatus 10 according to the embodiment of the present invention.

As shown in FIG. 3, the weight measuring apparatus 10 includes a first arm 110, a second arm 120, a third arm 130, a pillar 140, and an alarm 300.

The first arm 110 is a bar-shaped member made of a metal. An example of the first arm 110 is a square bar made of aluminum. The first arm 110 has a through-hole penetrating two facing surfaces of the first arm 110. The through-hole is arranged horizontally in a direction perpendicular to a longitudinal direction of the first arm 110. A cross-sectional view of the through-hole has a shape of a bone, namely, a shape in which each of two ends is larger than a central part between the two ends. More specifically, the first arm 110 forms a Roberval load cell.

The first arm 110 has a first fitting 111 at an distal end 110a of the first arm 110. The first arm 110 has a third measuring device 210 in a base end 110b of the first arm 110.

The first fitting 111 is a member by which the supply fluid container 20 is fit to the first arm 110. More specifically, the first fitting 111 is a wire member made of a metal to hang the supply fluid container 20. It should be noted that the material and the shape of the first fitting 111 are not limited to metal and wire, but any material and shape are possible for the first fitting 111 as long as the first fitting 111 can fit the supply fluid container 20.

The third measuring device 210 is a device that measures, based on a change of the first arm 110, a weight of the supply fluid container 20 hanged by the first fitting 111. More specifically, the third measuring device 210 measures a weight of the supply fluid container 20 hanged by the first fitting 111, based on a strain value of the first arm 110.

More specifically, if the supply fluid container 20 is hanged by the first fitting 111, the first arm 110 is strained due to the through-hole in the first arm 110. The third measuring device 210 calculates a weight of the supply fluid container 20 based on the strain value of the first arm 110, thereby measuring a weight of the supply fluid container 20.

It should be noted that the material and the shape of the first arm 110 are not limited to the metal bar, but any material and shape are possible for the first arm 110 as long as the third measuring device 210 can measure a weight of the supply fluid container 20.

The second arm 120 is a bar-shaped member made of a metal. Likewise the first arm 110, the second arm 120 also has a through-hole. Since the material and shape of the second arm 120 are the same as those of the first arm 110, they will not be described in detail again.

Then, the second arm 120 has an distal end 120a connected with the base end 110b of the first arm 110. The second arm 120 has a second fitting 121 at the distal end 120a of the second arm 120. The second arm 120 has a first measuring device 220 at a base end 120b of the second arm 120.

The second fitting 121 is a member by which the filtrate container 30 is fit to the second arm 120. More specifically, the second fitting 121 is a wire member made of a metal to hang the filtrate container 30. It should be noted that the material and the shape of the second fitting 121 are not limited to metal and wire, but any material and shape are possible for the second fitting 121 as long as the second fitting 121 can fit the filtrate container 30.

The first measuring device 220 measures a total weight of the supply fluid container 20 and the filtrate container 30, based on a change of the second arm 120. Here, the supply fluid container 20 is hanged by the first fitting 111 and the filtrate container 30 is hanged by the second fitting 121. As a result, the first measuring device 220 outputs the measured weight as a first total weight. In short, the first measuring device 220 measures the total weight based on a strain value of the second arm 120.

More specifically, when the supply fluid container 20 and the filtrate container 30 are hanged, the second arm 120 is strained due to the through-hole in the second arm 120. The first measuring device 220 measures the first total weight based on the strain value of the second arm 120, and outputs the first total weight.

It should be noted that the material and the shape of the second arm 120 are not limited to the same as those of the first arm 110, but any material and shape are possible for the second arm 120 as long as the first measuring device 220 can measure the total weight based on the strain value.

The third arm 130 is a bar-shaped member made of a metal. Likewise the first arm 110, the third arm 130 also has a through-hole. Since the material and shape of the third arm 130 are the same as those of the first arm 110, they will not be described in detail again.

Then, the third arm 130 has an distal end 130a connected with the base end 120b of the second arm 120. The third arm 130 also has a second measuring device 230 at a base end 130b of the third arm 130.

The second measuring device 230 measures a total weight of the supply fluid container 20 and the filtrate container 30, based on a change of the third arm 130. Here, the supply fluid container 20 is hanged by the first fitting 111 and the filtrate container 30 is hanged by the second fitting 121. As a result, the second measuring device 230 outputs the measured weight as a second total weight. In short, the second measuring device 230 measures the total weight based on a strain value of the third arm 130.

More specifically, when the supply fluid container 20 and the filtrate container 30 are hanged, the third arm 130 is strained due to the through-hole in the third arm 130. The second measuring device 230 calculates the second total weight based on the strain value of the third arm 130, and outputs the second total weight.

It should be noted that the material and the shape of the third arm 130 are not limited to the same as those of the first arm 110, but any material and shape are possible for the third arm 130 as long as the second measuring device 230 can measure the total weight based on the strain value.

As described above, since the containers to be measured are not hanged from the third arm 130, a total weight measured by the first measuring device 220 in the second arm 120 is equal to a total weigh measured by the second measuring device 230 in the third arm 130. As a result, the two measuring devices can perform mutual monitoring (verification).

As described above, each of the measuring devices can measure a target weight based on a strain value of a corresponding arm. As a result, the measuring devices can measure the weights easily and with high accuracy. It should be noted that it has been described in the embodiment that each of the measuring devices is provided at the base end of the corresponding arm, but the present embodiment is not limited to the above structure and each of the measuring devices may be provided at any position as long as a strain can be measured with high accuracy. It should also be noted that the first arm 110, the second arm 120, and the third arm 130 may be different members or a single integrated member.

The pillar 140 is a member made of a metal extending in a vertical direction. An example of the pillar 140 is a bar-shaped member made of aluminum. The pillar 140 is connected with the base end 130b of the third arm 130 so that the pillar 140 and the third arm 130 are at right angles to each other. With the above structure, the pillar 140 supports the third arm 130. It should be noted that the material and the shape of the pillar 140 are not limited to the metal bar, but any material and shape are possible for the pillar 140 as long as the pillar 140 can support the third arm 130.

The alarm 330 performs alarming, when the first total weight measured by the first measuring device 220 and the second total weight measured by the second measuring device 230 have different values having a difference equal to or greater than a predetermined value. The alarm 330 will be described in more detail later.

Figure 4:
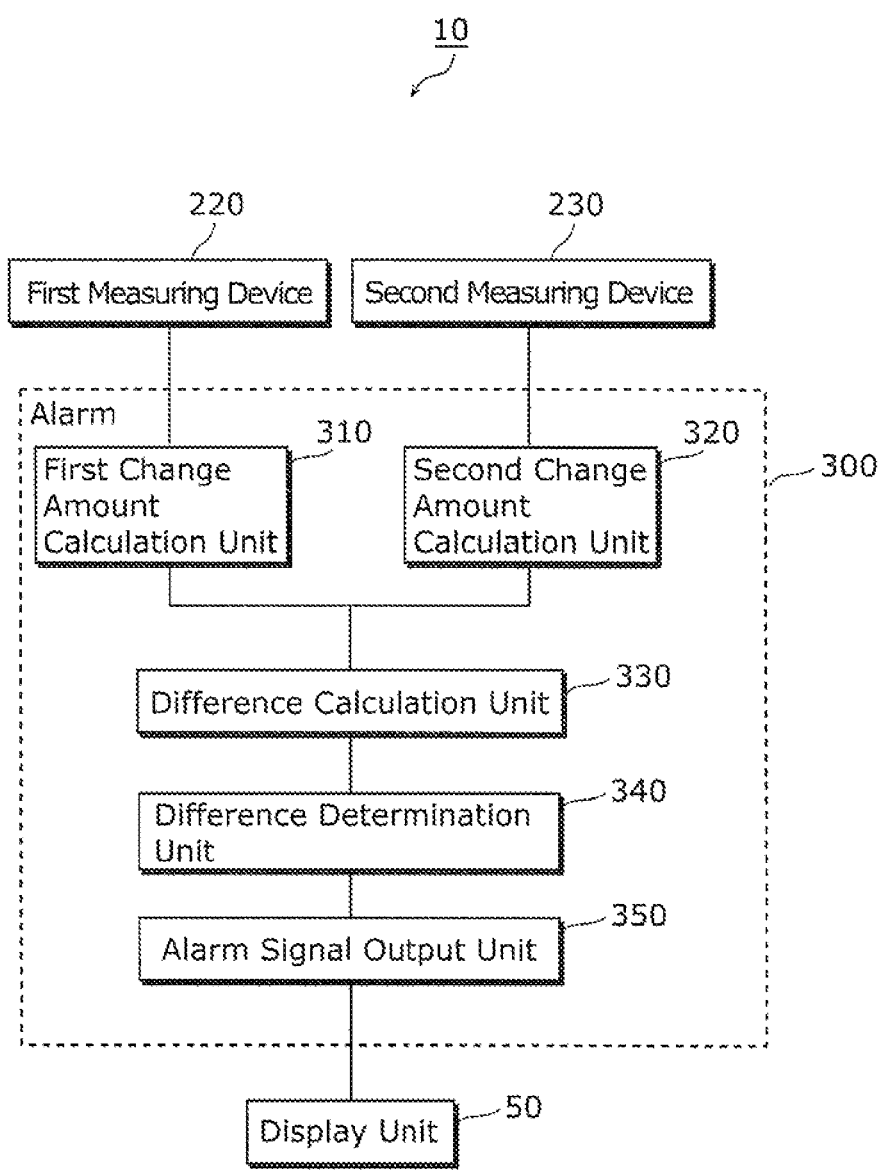
FIG. 4 is a block diagram showing a functional structure of the weight measuring apparatus according to the embodiment of the present invention.

FIG. 4 is a block diagram showing a functional structure of the weight measuring apparatus 10 according to the embodiment of the present invention.

The weight measuring apparatus 10 provides the alarm 300 with the first total weight measured by the first measuring device 220 and the second total weight measured by the second measuring device 230. The alarm 330 thereby displays alarm notification on the display unit 50 in order to alarm the user.

As shown in FIG. 4, the alarm 330 includes a first change is amount calculation unit 310, a second change amount calculation unit 320, a difference calculation unit 330, a difference determination unit 340, and an alarm signal output unit 350.

The first change amount calculation unit 310 calculates a first change amount that is an amount having changed since an initial state of the first total weight measured by the first measuring device 220. More specifically, the first change amount calculation unit 310 subtracts an initial value from a current value of the first total weight measured by the first measuring device 220, thereby calculating the first change amount.

The second change amount calculation unit 320 calculates a second change amount that is an amount having changed since an initial state of the second total weight measured by the second measuring device 230. More specifically, the second change amount calculation unit 320 subtracts an initial value from a current value of the second total weight measured by the second measuring device 230, thereby calculating the second change amount.

The difference calculation unit 330 calculates a difference between the first change amount calculated by the first change amount calculation unit 310 and the second change amount calculated by the second change amount calculation unit 320. More specifically, the difference calculation unit 330 subtracts a value of the second change amount from a value of the first change amount to calculate the difference. If a value of the difference is a minus value, the difference calculation unit 330 sets an absolute value of the difference to be the difference.

The difference determination unit 340 determines whether or not the difference calculated by the difference calculation unit 330 is equal to or greater than a predetermined value. In other words, if the difference is equal to or greater than the predetermined value, it means that at least one of the first measuring device 220 and the second measuring device 230 outputs a wrong value. Here, the predetermined value is a numeral value that can be set freely depending on the situation. The predetermined value is appropriately set depending on a measurement accuracy or sizes of the containers.

If the difference determination unit 340 determines that the difference is equal to or greater than the predetermined value, the alarm signal output unit 350 issues an alarm signal to the display unit 50. More specifically, if the difference is equal to or greater than the predetermined value, this means that at least one of the first measuring device 220 and the second measuring device 230 outputs a wrong value. Therefore, the alarm signal output unit 350 issues the alarm signal to the display unit 50 to display alarm notification.

As described above, the display unit 50 displays the alarm notification notifying that at least one of the first measuring device 220 and the second measuring device 230 outputs a wrong value.

Next, an example of processing performed by the weight measuring apparatus 10 is described.

Figure 5:
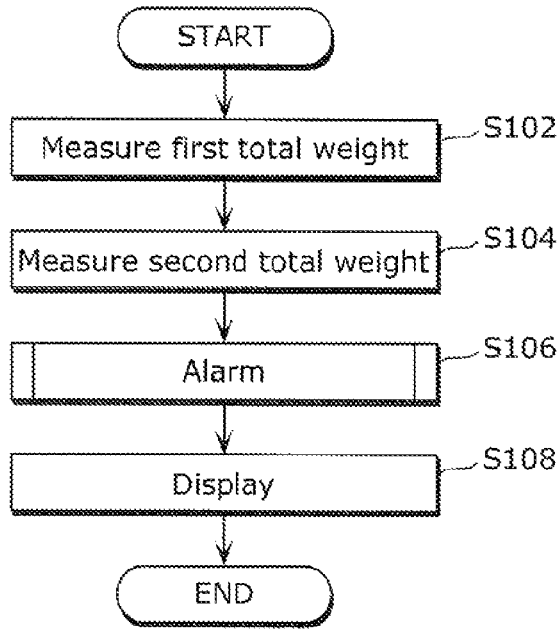
FIG. 5 is a flowchart of an example of processing performed by the weight measuring apparatus according to the embodiment of the present invention.

FIG. 5 is a flowchart of an example of processing performed by the weight measuring apparatus 10 according to the embodiment of the present invention.

First, the first measuring device 220 measures the first total weight (S102). In more detail, the first measuring device 220 measures a total weight of the containers as the first total weight, and provides the first total weight to the alarm 330.

Furthermore, the second measuring device 230 measures the second total weight (S104). In more detail, the second measuring device 230 measures a total weight of the containers as the second total weight, and provides the second total weight to the alarm 330.

Then, the alarm 300 performs alarming, if the first total weight and the second total weight have different values having a difference equal to or greater than a predetermined value (S106). In more detail, the alarm 300 issues an alarm signal to the display unit 50. The alarm processing performed by the alarm 330 will be described in more detail later.

Then, the display unit 50 displays alarm notification based on the alarm signal (S108).

Thereby, the weight measuring apparatus 10 completes the processing.

Next, the alarm processing performed by the alarm 330 (S106 in FIG. 5) is described in more detail.

Figure 6:
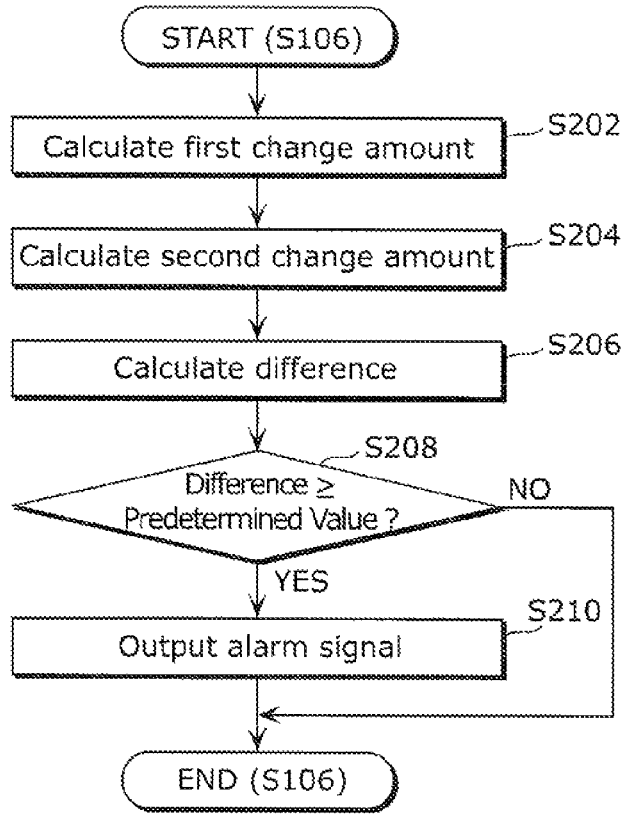
FIG. 6 is a flowchart of processing performed by an alarm to alarm a user.

FIG. 6 is a flowchart of the alarm processing performed by the alarm 330 (S106 in FIG. 5).

The first change amount calculation unit 310 calculates a first change amount that is an amount having changed since an initial state of the first total weight measured by the first measuring device 220 (S202).

Furthermore, the second change amount calculation unit 320 calculates a second change amount that is an amount having changed since an initial state of the second total weight measured by the second measuring device 230 (S204).

Then, the difference calculation unit 330 calculates a difference between the first change amount and the second change amount (S206).

The difference determination unit 340 determines whether or not the difference calculated by the difference calculation unit 330 is equal to or greater than a predetermined value (S208).

If the difference determination unit 340 determines that the difference calculated by the difference calculation unit 330 is equal to or greater than the predetermined value (YES at S208), then the alarm signal output unit 350 issues an alarm signal for alarming to the display unit 50 (S210).

On the other hand, if the difference determination unit 340 determines that the difference calculated by the difference calculation unit 330 is less than the predetermined value (NO at S208), then the alarm 330 completes the processing.

As described above, the alarm processing performed by the alarm 300 (S106 in FIG. 5) is completed.

The following describes effects of the weight measuring apparatus 10 according to the embodiment of the present invention.

Figure 7:
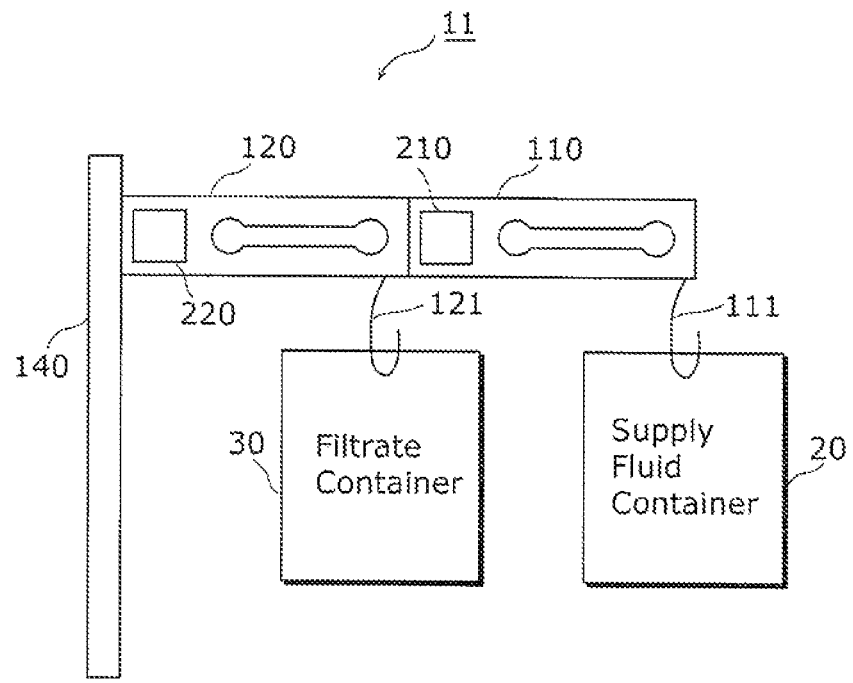
FIG. 7 is a diagram for explaining effects of the weight measuring apparatus according to the embodiment of the present invention.

FIG. 7 is a diagram for explaining the effects of the weight measuring apparatus 10 according to the embodiment of the present invention. More specifically, FIG. 7 shows a structure of the conventional weight measuring apparatus 11.

As shown in FIG. 7, the conventional weight measuring apparatus 11 does not include the third arm 130 having the second measuring device 230 at the base end 130b shown in FIG. 3.

On the other hand, in the weight measuring apparatus 10 according to the embodiment of the present invention, each of two measuring devices, which are the first measuring device 220 and the second measuring device 230, measures a total weight of the supply fluid container 20 and the filtrate container 30, thereby performing mutual monitoring. When the measured results of the first measuring device 220 and the second measuring device 230 have different values having a difference equal to or greater than a predetermined value, alarm is performed.

Therefore, in the weight measuring apparatus 10 according to the embodiment of the present invention, even if a trouble or deterioration of measurement accuracy occurs in the first measuring device 220 or the second measuring device 230, it is possible to immediately notice the trouble or the measurement accuracy deterioration. As a result, safety can be ensured.

Although the weight measuring apparatus according to the present invention have been described with reference to the embodiment as above, the present invention is not limited to the embodiment.

The embodiment disclosed above is merely exemplary in every aspect and does not limit the present invention. The scope of the present invention is indicated not by the above description but by the appended claims. Any modifications in the embodiment are intended to have the same meaning and be included within the scope of the claims.

For example, it has been described in the embodiment that the first arm 110, the second arm 120, and the third 130 are connected to each other in a linear arrangement. However, the first arm 110, the second arm 120, and the third 130 are not limited to be connected to each other in the linear arrangement.

Figure 8:
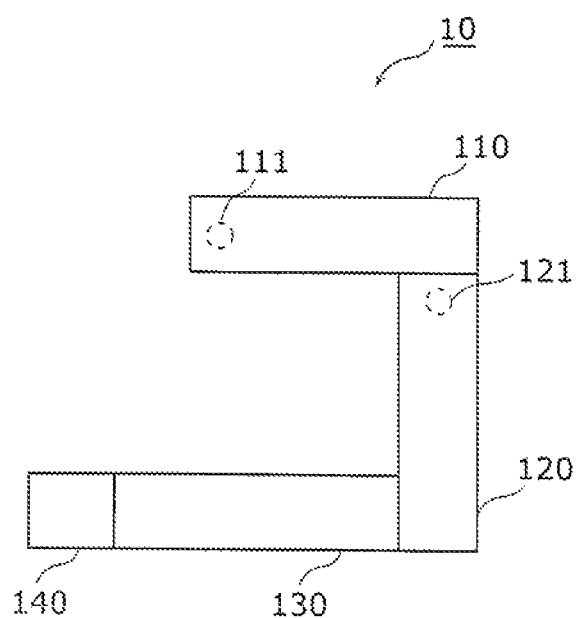
FIG. 8 is a diagram of a weight measuring apparatus according to a first variation of the embodiment of the present invention.

FIG. 8 is a diagram of the weight measuring apparatus 10 according to a first variation of the embodiment of the present invention.

As shown in FIG. 8, the first arm 110, the second arm 120, and the third 130 are connected to each other not in the linear arrangement, but in a U-shape arrangement. Even with the structure, the weight measuring apparatus 10 can offer the same functions and the same effects as those of the above-described embodiment.

It should also be noted that it has been described in the embodiment that the first arm 110, the second arm 120, and the third 130 are connected to each other to measure weights of the supply fluid container 20 and the filtrate container 30. However, the number of the arms is not limited to three. It may be two, or more than four. Especially, if the supply fluid container 20 is separated into a dialysate container 23 containing dialysate and a replacement fluid container 24 containing replacement fluid, four arms are necessary.

FIG. 9 is a diagram of the weight measuring apparatus 10 according to a second variation of the embodiment of the present invention.

As shown in FIG. 9, the first arm 110 consists of a fourth arm 112 and a fifth arm 114. Therefore, the weight measuring apparatus 10 includes four arms.

In the structure, the first arm 110 has the first fitting 111 to hang the supply fluid container 20 that consists of the dialysate container 23 and the replacement fluid container 24. More specifically, the first fitting 111 consists of a third fitting 113 and a fourth fitting 115. The third fitting 113 hangs the dialysate container 23, while the fourth fitting 115 hangs the replacement fluid container 24.

Here, a fourth measuring device 211 measures a weight of the dialysate container 23. A fifth measuring device 212 measures a total weight of the replacement fluid container 24 and the dialysate container 23.

The first measuring device 220 measures, as the first total weight, a total weight of (a) the dialysate container 23 hanged by the third fitting 113, (b) the replacement fluid container 24 hanged by the fourth fitting 115, and (c) the filtrate container 30 hanged by the second fitting 121.

The second measuring device 230 measures, as the second total weight, a total weight of (a) the dialysate container 23 hanged by the third fitting 113, (b) the replacement fluid container 24 hanged by the fourth fitting 115, and (c) the filtrate container 30 hanged by the second fitting 121.

Then, the alarm 300 performs alarming, if the first total weight and the second total weight have different values having a difference equal to or greater than a predetermined value.

It should be noted that it has described n the above-described embodiment that the first arm 110 has the distal end 110a having the first fitting 111, and has the base end 110b having the third measuring device 210, that the second arm 120 has the distal end 120a having the second fitting 121, and has the base end 120b having the first measuring device 220, and that the third arm 130 has the base end 130b having the second measuring device 230. However, the first fitting 111, the third measuring device 210, the second fitting 121, the first measuring device 220, and the second measuring device 230 are not necessarily provided at the above-described distal ends and base ends. They may be arranged at central parts of the arms. Furthermore, the third measuring device 210, the first measuring device 220, and the second measuring device 230 are not necessarily provided to the first arm 110, the second arm 120, and the third arm 130, respectively, as long as they can measure target weights.

It should also be noted that it has been described in the above-described embodiment that the supply fluid container 20 and the filtrate container 30 are hanged by the first arm 110 and the second arm 120, respectively, and the weight measuring apparatus 10 measures a weight of the fluids. However, the supply fluid container 20 and the filtrate container 30 are not necessarily hanged by the first arm 110 and the second arm 120, respectively, but may be placed on the first arm 110 and the second arm 120, respectively, so that the weight measuring apparatus 10 measures a weight of the fluids.

It should also be noted that it has been described in the above-described embodiment that the first measuring device 220, the second measuring device 230, and the third measuring device 210 measure the respective target weights based on strain values of the second arm 120, the third arm 130, and the first arm 110, respectively. However, it is also possible that the first measuring device 220, the second measuring device 230, and the third measuring device 210 measure weights by detecting torques caused in the second arm 120, the third arm 130, and the first arm 110, based on state changes of the second arm 120, the third arm 130, and the first arm 110, respectively.

It should also be noted that it has been described in the above-described embodiment that the alarm signal output unit 350 issues an alarm signal to the display unit 50 to cause the display unit 50 to display alarm notification. However, the alarm signal output unit 350 may issue the alarm signal to alarm by audio, or issue the alarm signal to stop blood purification or to adjust a flow rate of a supply fluid or filtrate.

INDUSTRIAL APPLICABILITY

The weight measuring apparatus included in the blood purification apparatus according to the present invention is useful as a weight measuring apparatus or the like that can ensure safety even if a trouble or deterioration of measurement accuracy occurs in purification of blood of a patient having, for example, renal function insufficiency.

NUMERICAL REFERENCES 1 blood purification apparatus
10 weight measuring apparatus
20 supply fluid container
21 dialysate pump
22 replacement fluid pump
23 dialysate container
24 replacement fluid container
30 filtrate container
31 filtrate pump
40 blood purifier
50 display unit
110 first arm
111 first fitting
112 fourth arm
113 third fitting
114 fifth arm
115 fourth fitting
120 second arm
121 second fitting
130 third arm
140 pillar
210 third measuring device
211 fourth measuring device
212 fifth measuring device
220 first measuring device
230 second measuring device
300 alarm
310 first change amount calculation unit
320 second change amount calculation unit
330 difference calculation unit
340 difference determination unit
350 alarm signal output unit

The invention claimed is:

1. A weight measuring apparatus to which containers containing fluids are fit, said weight measuring apparatus measuring a weight of the fluids, said weight measuring apparatus comprising:
  a first arm having a first fitting to fit a first container containing a first fluid;
  a second arm having a second fitting to fit a second container containing a second fluid, said second arm being connected to said first arm;
  a first measuring device that measures, as a first total weight, a total weight based on a change of said second arm, the total weight being a total of a weight of said first container fit by said first fitting and a weight of said second container fit by said second fitting;
  a third arm connected to said second arm;
  a second measuring device measuring, as a second total weight, the total weight based on a change of said third arm; and
  an alarm alarming, when the first total weight and the second total weight have different values having a difference equal to or greater than a predetermined value.

2. The weight measuring apparatus according to claim 1, wherein said alarm includes:
  a first change amount calculation unit configured to calculate a first change amount that is an amount having changed since an initial state of the first total weight;
  a second change amount calculation unit configured to calculate a second change amount that is an amount having changed since an initial state of the second total weight;

a difference calculation unit configured to calculate a difference between the first change amount and the second change amount;
a difference determination unit configured to determine whether or not the difference is equal to or greater than the predetermined value; and
an alarm signal output unit configured to issue an alarm signal to alarm, when said difference determination unit determines that the difference is equal to or greater than the predetermined value.

3. The weight measuring apparatus according to claim 1, further comprising
a third measuring device measuring a weight of said first container fit by said first fitting, based on a change of said first arm.

4. The weight measuring apparatus according to claim 3, further comprising
a pillar supporting said third arm,
wherein said first arm has an distal end having said first fitting,
said second arm has an distal end having said second fitting, the distal end being connected to a base end of said first arm,
said third arm has an distal end connected to a base end of said second arm, and a base end connected to said pillar,
said third measuring device measures the weight of said first container based on a strain value of said first arm,
said first measuring device measures the first total weight based on a strain value of said second arm, and
said second measuring device measures the second total weight based on a strain value of said third arm.

5. The weight measuring apparatus according to claim 1, wherein said first arm has said first fitting to fit the first container containing the first fluid, the first fluid being used for blood purification, and
said second arm has said second fitting to fit the second container containing the second fluid, the second fluid being used for blood purification.

* * * * *